(12) United States Patent
Nakatani et al.

(10) Patent No.: US 9,663,563 B2
(45) Date of Patent: May 30, 2017

(54) AQUEOUS LIQUID COMPOSITION

(71) Applicant: Dainippon Sumitomo Pharma Co., Ltd., Osaka-shi, Osaka (JP)

(72) Inventors: Tomomi Nakatani, Ibaraki (JP); Koichi Saito, Ibaraki (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 14/204,618

(22) Filed: Mar. 11, 2014

(65) Prior Publication Data

US 2014/0271693 A1    Sep. 18, 2014

Related U.S. Application Data

(60) Provisional application No. 61/777,423, filed on Mar. 12, 2013.

(51) Int. Cl.

| | | |
|---|---|---|
| *C07K 7/08* | (2006.01) | |
| *C07K 7/06* | (2006.01) | |
| *C07K 14/47* | (2006.01) | |
| *A61K 9/00* | (2006.01) | |
| *A61K 47/12* | (2006.01) | |
| *A61K 39/00* | (2006.01) | |
| *C07K 7/00* | (2006.01) | |
| *A61K 38/00* | (2006.01) | |
| *A61K 9/08* | (2006.01) | |

(52) U.S. Cl.
CPC ........ *C07K 14/4748* (2013.01); *A61K 9/0019* (2013.01); *A61K 39/0011* (2013.01); *A61K 47/12* (2013.01); *A23V 2200/308* (2013.01); *A61K 9/08* (2013.01); *A61K 38/00* (2013.01); *C07K 7/00* (2013.01)

(58) Field of Classification Search
CPC ...... A61K 2300/00; A61K 47/12; A61K 8/64; A61K 9/0019; A01N 25/02; C11D 7/265; C11D 3/2086; C11D 3/38663; C07K 7/06; C07K 7/08
See application file for complete search history.

(56) References Cited

U.S. PATENT DOCUMENTS

| | | | | |
|---|---|---|---|---|
| 5,272,135 | A * | 12/1993 | Takruri | 514/2.4 |
| 7,030,212 | B1 * | 4/2006 | Sugiyama et al. | 530/328 |
| 2004/0097703 | A1 | 5/2004 | Sugiyama | |
| 2004/0242444 | A1 * | 12/2004 | Behler et al. | 510/130 |
| 2006/0205667 | A1 | 9/2006 | Sugiyama et al. | |
| 2006/0217297 | A1 | 9/2006 | Sugiyama et al. | |
| 2008/0026046 | A1 | 1/2008 | Skufca et al. | |
| 2009/0075860 | A1 | 3/2009 | Yamaguchi et al. | |
| 2009/0099090 | A1 | 4/2009 | Sugiyama et al. | |
| 2009/0143291 | A1 | 6/2009 | Sugiyama et al. | |
| 2010/0028372 | A1 | 2/2010 | Jezek | |
| 2010/0055129 | A1 | 3/2010 | Refaeli et al. | |
| 2010/0062010 | A1 | 3/2010 | Nishihara et al. | |
| 2010/0190163 | A1 | 7/2010 | Sugiyama | |
| 2010/0255020 | A1 | 10/2010 | Miyakawa et al. | |
| 2011/0070251 | A1 | 3/2011 | Sugiyama | |
| 2011/0318380 | A1 | 12/2011 | Brix et al. | |
| 2012/0004306 | A1 | 1/2012 | Miura et al. | |
| 2012/0294829 | A1 | 11/2012 | Lee et al. | |
| 2013/0064812 | A1 | 3/2013 | Gallatin et al. | |
| 2014/0023670 | A1 | 1/2014 | Sugiyama | |
| 2015/0150975 | A1 * | 6/2015 | Tanaka | A61K 47/12 424/185.1 |
| 2015/0196564 | A1 | 7/2015 | Gallatin et al. | |

FOREIGN PATENT DOCUMENTS

| | | |
|---|---|---|
| EP | 0 969 089 A1 | 1/2000 |
| EP | 2762152 A1 | 8/2014 |
| EP | 2762159 A1 | 8/2014 |
| EP | 2974734 A1 | 1/2016 |
| JP | H03-063233 A | 3/1991 |
| JP | H06-284886 A | 10/1994 |
| JP | 2000-053584 A | 2/2000 |
| JP | 2000-212073 A | 8/2000 |
| JP | 2007-509101 A | 4/2007 |

(Continued)

OTHER PUBLICATIONS

Partidos et al. Applying peptide antigens onto bare skin: induction of humoral and cellular immune responses and potential for vaccination. J Control Release. Dec. 13, 2002;85(1-3):27-34.*
Czerkinsky et al. Topical immunization strategies. Mucosal Immunol. Nov. 2010;3(6):545-55.*
Japanese Patent Office, International Search Report in Japanese Patent Application No. PCT/JP2014/056273 (Jun. 3, 2014).
Melief et al., *Current Opinion in Immunology*, 5(5): 709-713 (1993).
Mescher, *Immunological Reviews*, 146(1): 177-210 (1995).
Nanda et al., *Cell*, 82(1): 13-17 (Jul. 14, 1995).
Oji et al., *Cancer Science*, 95(7): 583-587 (Jul. 2004).

(Continued)

*Primary Examiner* — Satyanarayana R Gudibande
*Assistant Examiner* — Jia-Hai Lee
(74) *Attorney, Agent, or Firm* — Leydig, Voit & Mayer, Ltd.

(57) ABSTRACT

The invention provides an aqueous liquid composition comprising a WT1 protein-derived cancer antigen peptide, wherein the peptide is stabilized. The aqueous liquid composition contains a peptide and an excipient, and has a pH of 3-6. The peptide has the amino acid sequence Arg-Met-Phe-Pro-Asn-Ala-Pro-Tyr-Leu (SEQ ID NO: 1), wherein optionally 1 to 3 amino acids are deleted, substituted and/or added, such that the peptide has a cytotoxic T cell-inducing ability. The excipient is (a) an alpha hydroxyl acid selected from glycolic acid, lactic acid, malic acid, tartaric acid, citric acid and pharmacologically acceptable salts thereof, (b) a dicarboxylic acid selected from malonic acid, succinic acid, glutaric acid, maleic acid and pharmacologically acceptable salts thereof, and/or (c) methionine.

17 Claims, 1 Drawing Sheet

(56) References Cited

FOREIGN PATENT DOCUMENTS

| | | |
|---|---|---|
| JP | 2008-127277 A | 6/2008 |
| JP | 2010-515713 A | 5/2010 |
| JP | 2011-030981 A | 2/2011 |
| JP | 2012-501347 A | 1/2012 |
| JP | 2004-010511 A | 1/2014 |
| WO | WO 00/06602 A1 | 2/2000 |
| WO | WO 00/18795 A2 | 4/2000 |
| WO | WO 02/079253 A1 | 10/2002 |
| WO | WO 03/106682 A1 | 12/2003 |
| WO | WO 2004/026897 A1 | 4/2004 |
| WO | WO 2004/063217 A1 | 7/2004 |
| WO | WO 2006/118246 A1 | 11/2006 |
| WO | WO 2007/063903 A1 | 6/2007 |
| WO | WO 2008/108257 A1 | 9/2008 |
| WO | WO 2009/066462 A1 | 5/2009 |
| WO | WO 2009-072610 A1 | 6/2009 |
| WO | WO 2010/037395 A2 | 4/2010 |
| WO | WO 2010/103845 A1 | 9/2010 |
| WO | WO 2011/090305 A2 | 7/2011 |
| WO | WO 2012/125510 A1 | 9/2012 |

OTHER PUBLICATIONS

Pardoll, *Current Opinion in Immunology*, 5(5): 719-725 (1993).
Rauscher III, *FASEB*, 7: 896-903 (1993).
Sugiyama, *International Journal of Hematology*, 73(2): 177-187 (2001).
European Patent Office, Supplementary European Search Report in European Patent Application No. 13813675 (Mar. 9, 2016).
Japanese Patent Office, International Search Report in International Patent Application No. PCT/JP2013/068182 (Oct. 8, 2013).
U.S. Appl. No. 14/412,148, filed Dec. 30, 2014.

\* cited by examiner

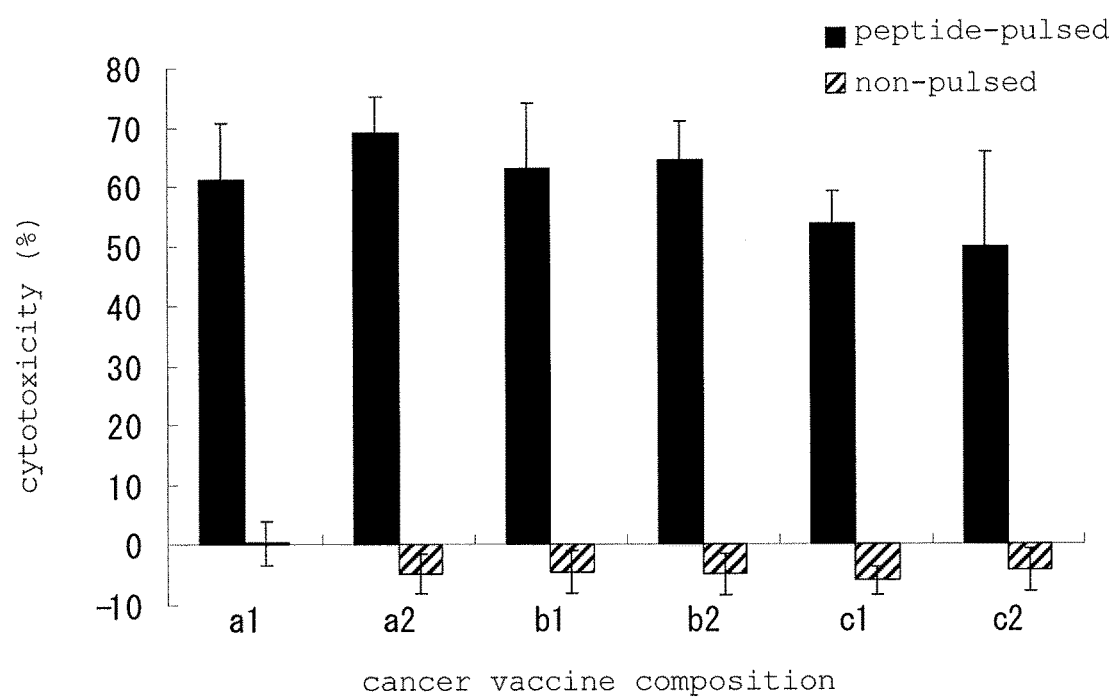

AQUEOUS LIQUID COMPOSITION

CROSS-REFERENCE TO RELATED APPLICATIONS

This patent claims the benefit of U.S. Provisional Patent Application No. 61/777,423, filed on Mar. 12, 2013, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 5,182 bytes ASCII (Text) file named "716371SequenceListing.txt," created Mar. 11, 2014.

TECHNICAL FIELD OF THE INVENTION

The present invention belongs to the field of cancer immunotherapy, and relates to an aqueous liquid composition comprising WT1 protein-derived cancer antigen peptide having a cytotoxic T cell-inducing activity, and to stabilization of drug by the composition.

BACKGROUND OF THE INVENTION

Generally, the WT1 protein-derived cancer antigen peptide is a partial peptide derived from human WT1 protein consisting of 449 amino acids (SEQ ID NO: 2), and is specifically a peptide consisting of 8-12 amino acids or a dimer thereof. It is presented to a major histocompatibility complex (MHC) class I antigen, and includes a peptide which is antigen-recognized by cytotoxic T cell (cytotoxic T-lymphocyte, hereinafter to be referred to as CTL). MHC in human is called human leukocyte antigen (HLA).

Among the WT1 protein-derived partial peptides, a partial peptide consisting of 9 amino acids and shown by the sequence $WT1_{126-134}$ peptide Arg-Met-Phe-Pro-Asn-Ala-Pro-Tyr-Leu (SEQ ID NO: 1), and a modified peptide, wherein partial amino acid(s) is(are) modified (modified peptide), have been reported to be useful as peptides that bind to HLA to induce CTL (see patent documents 1-3, non-patent document 1).

A cancer antigen protein and a cancer antigen peptide, which are generally used for cancer vaccine, are administered with an adjuvant (immunopotentiating agent) in many cases to induce CTL more efficiently.

However, it is often difficult to maintain stability, particularly stability in water, of the formulations comprising these proteins and peptides. Therefore, the formulations removed water by freeze-drying are generally selected. Nevertheless, freeze-dried formulations are disadvantageous from the aspects of production and cost, and also require an operation when in use such as adding water and the like.

In view of the above, it is significant to develop a stable aqueous liquid composition that enables easy combination of a cancer antigen protein or cancer antigen peptide with various adjuvants depending on the object of use.

As for the stabilization of a liquid, a freeze-dried formulation containing citric acid or methionine as a stabilizer of gonadotropin (see patent document 4), a formulation containing methionine as a stabilizer of G-CSF (see patent document 5), and a formulation having pH 4 or below and containing succinic acid or tartaric acid as a stabilizer of G-CSF (see patent document 6) are disclosed.

Furthermore, a formulation containing, as stabilizers of modified factor VIII polypeptide in solution, (1) pH adjuster to fall within the range of about 4.0-about 8.0, (2) an antioxidant, and (3) calcium salt, magnesium salt is disclosed (see patent document 7). In addition, a formulation with improved stability, which contains a physiologically active medicament, methionine and a novel erythropoiesis stimulating protein is disclosed (see patent document 8).

However, a stable aqueous liquid composition containing a partial peptide having the sequence shown by SEQ ID NO: 1 or a modified peptide thereof, which is of interest in the present invention, has not been known.

DOCUMENT LIST

Patent Documents patent document 1: WO00/06602
patent document 2: WO00/18795
patent document 3: WO2009/072610
patent document 4: JP-A-H10-203997
patent document 5: JP-A-2000-247903
patent document 6: WO2005/39620
patent document 7: WO03/55511
patent document 8: WO03/20299

Non-Patent Document non-patent document 1: Written opinion in examination of EP-B-1127068

SUMMARY OF THE INVENTION

Problems to be Solved by the Invention

The problem of the present invention is to provide a aqueous liquid composition improved the stability of a partial peptide having the sequence shown by SEQ ID NO: 1 or a modified peptide of said peptide, which can be used for the preparation of a cancer vaccine formulation comprising the above-mentioned peptide.

Means of Solving the Problems

The present inventors have conducted intensive studies in an attempt to solve the above-mentioned problem and found that a major degradation product in an aqueous liquid composition comprising a partial peptide having the sequence shown by SEQ ID NO: 1 or a modified peptide of said peptide (hereinafter sometimes to be simply referred to as the peptide of the present invention) results from oxidation of a methionine residue comprised in the peptide. Furthermore, they have found that oxidation of the methionine residue of said peptide is suppressed by adding a particular excipient as a stabilizer, and an aqueous liquid composition superior in formulation stability is obtained by adjusting the composition to have a particular, pH, which resulted in the completion of the present invention.

Accordingly, the present invention relates to the following.

Item 1. An aqueous liquid composition comprising the peptide and the excipient, and having a pH of 3-6:
wherein
the peptide is selected from the group consisting of the following (A) and (B), (A) a peptide consisting of the amino acid sequence shown by Arg-Met-Phe-Pro-Asn-Ala-Pro-Tyr-Leu (SEQ ID NO: 1), and
(B) a peptide consisting of the amino acid sequence shown by SEQ ID NO: 1, wherein 1 to 3 amino acids are deleted, substituted and/or added, and having a cytotoxic T cell-inducing ability; and
the excipient comprises one or more kinds selected from the group consisting of the following (C), (D) and (E),
(C) one or more kinds of alpha hydroxy acids selected from the group consisting of glycolic acid, lactic acid, malic acid, tartaric acid, citric acid and pharmacologically acceptable salts thereof,
(D) one or more kinds of dicarboxylic acids selected from the group consisting of malonic acid, succinic acid, glutaric acid, maleic acid and pharmacologically acceptable salts thereof, and
(E) methionine.

Item 2. The aqueous liquid composition according to item 1, wherein the excipient comprises one or more kinds selected from the group consisting of the following (C), (D) and (E):
(C) one or more kinds of alpha hydroxy acids selected from the group consisting of glycolic acid, lactic acid, malic acid, tartaric acid and pharmacologically acceptable salts thereof,
(D) one or more kinds of dicarboxylic acids selected from the group consisting of succinic acid, maleic acid and pharmacologically acceptable salts thereof, and
(E) methionine.

Item 3. The aqueous liquid composition according to item 1 or 2, wherein (B) is Phe-Met-Phe-Pro-Asn-Ala-Pro-Tyr-Leu (FMFPNAPYL) (SEQ ID NO: 3), Arg-Met-Met-Pro-Asn-Ala-Pro-Tyr-Leu (RMMPNAPYL) (SEQ ID NO: 4), Arg-Met-Phe-Pro-Asn-Ala-Pro-Tyr-Val (RMFPNAPYV) (SEQ ID NO: 5), Tyr-Met-Phe-Pro-Asn-Ala-Pro-Tyr-Leu (YMFPNAPYL) (SEQ ID NO: 6), or Ala-Arg-Met-Phe-Pro-Asn-Ala-Pro-Tyr-Leu (ARMFPNAPYL) (SEQ ID NO: 7).

Item 4. The aqueous liquid composition according to item 1 or 2, wherein the peptide comprising of the amino acid sequence shown by (A) Arg-Met-Phe-Pro-Asn-Ala-Pro-Tyr-Leu (SEQ ID NO: 1).

Item 5. The aqueous liquid composition according to any one of items 1-4, wherein the excipient comprises both (C) and (E).

Item 6. The aqueous liquid composition according to any one of items 1-5, wherein the excipient comprises both (C) and (E), and (C) is one or more kinds of alpha hydroxy acids selected from the group consisting of glycolic acid, lactic acid, malic acid, tartaric acid and pharmacologically acceptable salts thereof.

Item 7. The aqueous liquid composition according to any one of items 1-6, wherein the excipient comprises both (C) and (E), and (C) is one or more kinds of alpha hydroxy acids selected from the group consisting of glycolic acid and a pharmacologically acceptable salt thereof.

Item 8. The aqueous liquid composition according to any one of items 1-6, wherein the excipient comprises both (C) and (E), and (C) is one or more kinds of alpha hydroxy acids selected from the group consisting of lactic acid and a pharmacologically acceptable salt thereof.

Item 9. The aqueous liquid composition according to any one of items 1-6, wherein the excipient comprises both (C) and (E), and (C) is one or more kinds of alpha hydroxy acids selected from the group consisting of malic acid and a pharmacologically acceptable salt thereof.

Item 10. The aqueous liquid composition according to any one of items 1-6, wherein the excipient comprises both (C) and (E), and (C) is one or more kinds of alpha hydroxy acids selected from the group consisting of tartaric acid and a pharmacologically acceptable salt thereof.

Item 11. The aqueous liquid composition according to any one of items 1-4, wherein the excipient comprises both (D) and (E).

Item 12. The aqueous liquid composition according to item 1, 2, 3, 4 or 11, wherein the excipient comprises both (D) and (E), and (D) is one or more kinds of dicarboxylic acids selected from the group consisting of succinic acid and a pharmacologically acceptable salt thereof.

Item 13. The aqueous liquid composition according to item 1, 2, 3, 4 or 11, wherein the excipient comprises both (D) and (E), and (D) is one or more kinds of dicarboxylic acids selected from the group consisting of maleic acid and a pharmacologically acceptable salt thereof.

Item 14. The aqueous liquid composition according to any one of items 1-4, wherein the excipient comprises all of (C), (D) and (E).

Item 15. The aqueous liquid composition according to item 1, 2, 3, 4 or 14, wherein the excipient comprises all of (C), (D) and (E), (C) is one or more kinds of alpha hydroxy acids selected from the group consisting of glycolic acid, lactic acid, malic acid, tartaric acid and pharmacologically acceptable salts thereof, and (D) is one or more kinds of dicarboxylic acids selected from succinic acid, maleic acid and pharmacologically acceptable salts thereof.

Item 16. The aqueous liquid composition according to any one of items 1-15, wherein the content per volume of alpha hydroxy acid is 1-100 mM or the content per volume of dicarboxylic acid is 10-100 mM.

Item 17. The aqueous liquid composition according to any one of items 1-16, wherein the content per volume of methionine is 1-300 mM.

Item 18. The aqueous liquid composition according to any one of items 1-17, which has a pH of 4-5.

Item 19. A method of improving stability of a peptide in an aqueous liquid composition by adding an excipient:
wherein
the peptide is selected from the group consisting of the following (A) and (B),
(A) a peptide consisting of the amino acid sequence shown by Arg-Met-Phe-Pro-Asn-Ala-Pro-Tyr-Leu (SEQ ID NO: 1), and
(B) a peptide consisting of the amino acid sequence shown by SEQ ID NO: 1, wherein 1 to 3 amino acids are deleted, substituted and/or added, and having a cytotoxic T cell-inducing ability; and
the excipient comprises one or more kinds selected from the group consisting of the following (C), (D) and (E),
(C) one or more kinds of alpha hydroxy acids selected from the group consisting of glycolic acid, lactic acid, malic acid, tartaric acid, citric acid and pharmacologically acceptable salts thereof,
(D) one or more kinds of dicarboxylic acids selected from the group consisting of malonic acid, succinic acid, glutaric acid, maleic acid and pharmacologically acceptable salts thereof, and
(E) methionine.

Item 20. The method according to item 19, wherein the excipient comprises one or more kinds selected from the group consisting of the following (C), (D) and (E):
(C) one or more kinds of alpha hydroxy acids selected from the group consisting of glycolic acid, lactic acid, malic acid, tartaric acid and pharmacologically acceptable salts thereof, (D) one or more kinds of dicarboxylic acids selected from the group consisting of succinic acid, maleic acid and pharmacologically acceptable salts thereof, and
(E) methionine.

Item 21. The method according to item 19 or 20, wherein (B) is Phe-Met-Phe-Pro-Asn-Ala-Pro-Tyr-Leu (FMFPNAPYL) (SEQ ID NO: 3), Arg-Met-Met-Pro-Asn-Ala-Pro-Tyr-Leu (RMMPNAPYL) (SEQ ID NO: 4), Arg-Met-Phe-Pro-Asn-Ala-Pro-Tyr-Val (RMFPNAPYV) (SEQ ID NO: 5), Tyr-Met-Phe-Pro-Asn-Ala-Pro-Tyr-Leu (YMFPNAPYL) (SEQ ID NO: 6), or Ala-Arg-Met-Phe-Pro-Asn-Ala-Pro-Tyr-Leu (ARMFPNAPYL) (SEQ ID NO: 7).

Item 22. The method according to item 19 or 20, wherein the peptide consists of the amino acid sequence shown by (A) Arg-Met-Phe-Pro-Asn-Ala-Pro-Tyr-Leu (SEQ ID NO: 1).

Item 23. The method according to any one of items 19-22, wherein the excipient comprises both (C) and (E).

Item 24. The method according to any one of items 19-23, wherein both (C) and (E) are added as the excipient, and (C) is one or more kinds of alpha hydroxy acids selected from the group consisting of glycolic acid, lactic acid, malic acid, tartaric acid and pharmacologically acceptable salts thereof.

Item 25. The method according to any one of items 19-22, wherein both (D) and (E) are added as the excipient.

Item 26. The method according to item 19, 20, 21, 22 or 25, wherein both (D) and (E) are added as the excipient, and (D) is one or more kinds of dicarboxylic acids selected from the group consisting of succinic acid, maleic acid and pharmacologically acceptable salts thereof.

Item 27. The method according to any one of items 19-22, wherein the excipient comprises all of (C), (D) and (E).

Item 28. The method of item 19, 20, 21, 22 or 27, wherein the excipient comprises all of (C), (D) and (E), (C) is one or more kinds of alpha hydroxy acids selected from the group consisting of glycolic acid, lactic acid, malic acid, tartaric acid and pharmacologically acceptable salts thereof, and (D) is one or more kinds of dicarboxylic acids selected from the group consisting of succinic acid, maleic acid and pharmacologically acceptable salts thereof.

Effect of the Invention

Using the aqueous liquid composition of the present invention, an aqueous liquid composition stably comprising the peptide of the present invention having a cytotoxic T cell-inducing activity can be produced, and a cancer vaccine with superior stability can be formulated.

BRIEF DESCRIPTION OF THE DRAWING

The FIGURE shows the test results of CTL-inducing activity measured in Experimental Example 5.

DETAILED DESCRIPTION OF THE INVENTION

The embodiment of the present invention is explained in detail in the following.

In the present specification, a preferable embodiment of each exemplification may be combined with a preferable embodiment of other exemplification, or may be incorporated in the corresponding exemplification described in the aforementioned item 1-item 28.

The "aqueous liquid composition" of the present invention is a liquid for preparing a cancer vaccine, which contains water as the main solvent and can be mixed with various adjuvants. While water is generally used as the solvent, a pharmacologically acceptable solvent such as ethanol, propylene glycol, polyethylene glycol and the like can be partially mixed with water as long as the effect of the invention is not affected. Preferably, water alone is used as a solvent.

The "peptide" in the present invention is a cancer antigen peptide for preparing a cancer vaccine, and means a peptide selected from the group consisting of (A) "peptide consisting of the amino acid sequence shown by the sequence of Arg-Met-Phe-Pro-Asn-Ala-Pro-Tyr-Leu (SEQ ID NO 1)" and (B) "peptide wherein, in the amino acid sequence shown by SEQ ID NO: 1, 1 to 3 amino acids are deleted, substituted and/or added, and having a cytotoxic T cell-inducing ability". Preferred is a peptide consisting of the amino acid sequence shown by (A) Arg-Met-Phe-Pro-Asn-Ala-Pro-Tyr-Leu (SEQ ID NO: 1).

The "peptide consisting of the amino acid sequence shown by Arg-Met-Phe-Pro-Asn-Ala-Pro-Tyr-Leu (SEQ ID NO: 1)" is a protein which is a gene product of cancer suppressor gene WT1 of the Wilms' tumor, which is specifically a peptide consisting of the amino acid sequence consisting of 9 amino acids of Arg-Met-Phe-Pro-Asn-Ala-Pro-Tyr-Leu (SEQ ID NO: 1) (WT1$_{126-134}$ peptide) from the partial peptide consisting of 449 amino acids (SEQ ID NO: 2) derived from human WT1 protein. The peptide is presented to MHC class I antigen and antigen-recognized by CTL. The peptide can be produced by a known method (see patent documents 1, 2, 3, etc.).

As the "peptide consisting of the amino acid sequence shown by SEQ ID NO: 1 wherein 1 to 3 amino acids are deleted, substituted and/or added and having a cytotoxic T cell-inducing ability", a modified peptide which is the aforementioned partial peptide consisting of the amino acid sequence wherein 1 to 3 amino acids are deleted, substituted and/or added and binding to HLA to induce CTL can be mentioned. The number of the amino acids to be substituted is preferably 1 or 2, more preferably 1. A preferable substitution position is the 1-position, the 3-position or the 9-position. The number of the amino acids to be added (also including insertion) is preferably 1 or 2, more preferably 1. A preferable addition position is the 1-position. The number of the amino acids to be deleted is preferably 1. In the alteration, the amino acid to be added or amino acid to be substituted may be a non-natural amino acid other than the 20 kinds of amino acids encoded by the gene.

When the modified peptide contains at least one cysteine residue, two peptides (monomers) may be bonded to each other via a disulfide bond to form a dimer.

The modified peptide can be prepared by a method generally used in the technical field. For example, it can be synthesized by peptide synthesis methods described in Peptide Synthesis, Interscience, New York, 1966; The Proteins, Vol 2, Academic Press Inc., New York, 1976; peptide synthesis, Maruzen Co., 1975; Basics and Experiment of Peptide Synthesis, Maruzen Co. 1985; Development of Pharmaceutical Product sequel vol. 14•Peptide Synthesis, Hirokawa-Shoten Ltd., 1991 and the like.

Examples of the modified peptide include the following modified forms.

Phe-Met-Phe-Pro-Asn-Ala-Pro-Tyr-Leu (FMFPNAPYL) (SEQ ID NO: 3),
Arg-Met-Met-Pro-Asn-Ala-Pro-Tyr-Leu (RMMPNAPYL) (SEQ ID NO: 4),
Arg-Met-Phe-Pro-Asn-Ala-Pro-Tyr-Val (RMFPNAPYV) (SEQ ID NO: 5),

Tyr-Met-Phe-Pro-Asn-Ala-Pro-Tyr-Leu (YMFPNAPYL) (SEQ ID NO: 6), and Ala-Arg-Met-Phe-Pro-Asn-Ala-Pro-Tyr-Leu (ARMFPNAPYL) (SEQ ID NO: 7).

These modified forms are clearly modified peptides that bind to HLA to induce CTL, and can be prepared by a known method (see patent documents 1-3 and non-patent document 1).

As peptide to be the active ingredient in the present invention, a derivative of $WT1_{126-134}$ peptide shown by SEQ ID NO: 1 or a modified peptide thereof can also be used. For example, each peptide wherein various substances are bonded to the N-terminal and/or the C-terminal of the amino acid sequence thereof and the like can be mentioned. For example, amino acid, peptide, analogues thereof and the like may be bonded. When such substance is bonded to a peptide consisting of the amino acid sequence shown by SEQ ID NO: 1 or a modified peptide thereof, the substance is treated by, for example, an enzyme in the body and the like, or in the process of intracellular processing and the like, to finally prepare a peptide having a cytotoxic T cell-inducing ability, and induce a WT1 specific CTL reaction.

In the aqueous liquid composition of the present invention, the content of "peptide" per volume is not particularly defined, and may be a content relative to a volume acceptable from the aspect of pharmacology or property. Of the "peptide", for example, a preferable content of $WT1_{126-134}$ peptide (RMFPNAPYL) shown by SEQ ID NO: 1 is 0.01 mg/mL-200 mg/mL, more preferably 0.1 mg/mL-100 mg/mL, in an aqueous liquid composition, which can be selected according to the object of use.

In the present specification, the above-mentioned peptide has the N-terminal on the left side, and each amino acid symbol means the following amino acid residue.
Ala or A: alanine residue
Arg or R: arginine residue
Asn or N: asparagine residue
Asp or D: aspartic acid residue
Cys or C: cysteine residue
Gln or Q: glutamine residue
Glu or E: glutamic acid residue
Gly or G: glycine residue
His or H: histidine residue
Ile or I: isoleucine residue
Leu or L: leucine residue
Lys or K: lysine residue
Met or M: methionine residue
Phe or F: phenylalanine residue
Pro or P: proline residue
Ser or S: serine residue
Thr or T: threonine residue
Trp or W: tryptophan residue
Tyr or Y: tyrosine residue
Val or V: valine residue
Abu: 2-aminobutyric acid residue (to be also referred to as α-aminobutyric acid residue)
Orn: ornithine residue
Cit: citrulline residue In general, the "excipient" means a component other than an active ingredient, which is used for formulations. Examples of the "excipient" in the present invention (hereinafter sometimes to be conveniently referred to as "the excipient of the present invention") include one or more kinds of alpha hydroxy acids selected from the group consisting of glycolic acid, lactic acid, malic acid, tartaric acid, citric acid and pharmacologically acceptable salts thereof, one or more kinds of dicarboxylic acids selected from the group consisting of malonic acid, succinic acid, glutaric acid, maleic acid, fumaric acid and pharmacologically acceptable salts thereof, and methionine.

In general, "alpha hydroxy acid" is a carboxylic acid wherein a hydroxy group is also bonded to a carbon to which a carboxy group is bonded. Examples of the "alpha hydroxy acid" in the present invention include glycolic acid, lactic acid, malic acid, tartaric acid, citric acid and pharmacologically acceptable salts thereof. Examples of the pharmacologically acceptable salt include base addition salts. Examples of the base addition salt include aluminum salt, calcium salt, sodium salt, potassium salt and the like. Examples thereof include, but are not limited to, aluminum lactate, calcium lactate, sodium lactate, sodium malate, disodium malate, potassium hydrogen tartrate, sodium tartrate, potassium citrate, sodium citrate and the like. When two or more carboxy groups are present, a different base may be added to each carboxy group. Examples thereof include, but are not limited to, potassium sodium tartrate and the like. Moreover, it may be a hydrate. Examples thereof include, but are not limited to, calcium lactate hydrate, sodium malate ½ hydrate, disodium malate monohydrate, sodium tartrate dihydrate, potassium sodium tartrate tetrahydrate, citric acid hydrate, sodium citrate hydrate and the like. Using glycolic acid, lactic acid, malic acid, tartaric acid or citric acid, an aqueous liquid composition comprising the peptide of the present invention can be stabilized. One or more kinds of these can be used in combination. The alpha hydroxy acid to be used in the present invention is preferably glycolic acid, lactic acid, malic acid, tartaric acid or a pharmacologically acceptable salt thereof, more preferably tartaric acid or a pharmacologically acceptable salt thereof. While lactic acid, malic acid, and tartaric acid have optical isomers, an optically active form and racemate do not influence the effect of the invention. Tartaric acid is frequently used as an excipient for pharmaceutical products, and L-(+)tartaric acid described in the Japanese Pharmacopoeia (the 16th Edition) is preferable.

In the aqueous liquid composition of the present invention, while the content of "alpha hydroxy acid" per volume is not particularly specified, it is preferably 1-100 mM, more preferably 1-50 mM, most preferably 1-25 mM.

The "dicarboxylic acid" generally means a carboxylic acid having two carboxy groups in a molecule. Examples of the "dicarboxylic acid" in the present invention include malonic acid, succinic acid, glutaric acid, maleic acid, fumaric acid and pharmacologically acceptable salts thereof. Examples of the pharmacologically acceptable salt include base addition salts. Examples of the base addition salt include sodium salt, potassium salt and the like. Examples thereof include, but are not limited to, disodium malonate, sodium succinate, sodium glutarate, disodium fumarate and the like. Moreover, it may be a hydrate. Examples thereof include, but are not limited to, disodium malonate monohydrate, sodium succinate 6-hydrate, monosodium maleate trihydrate and the like. Using malonic acid, succinic acid, glutaric acid, maleic acid or fumaric acid, an aqueous liquid composition comprising the peptide of the present invention can be stabilized. One or more kinds of these can be used in combination. The dicarboxylic acid to be used in the present invention is preferably succinic acid, maleic acid, fumaric acid or a pharmacologically acceptable salt thereof.

In the aqueous liquid composition of the present invention, while the content of "dicarboxylic acid" per volume is not particularly defined, it is preferably 10-100 mM, more preferably 25-100 mM, most preferably 50-100 mM.

The "methionine" in the present invention is one of the essential amino acids, and is a hydrophobic amino acid comprising a sulfur atom in the side chain. While "methionine" has an optical isomer and includes a D form, an L form and a DL form, any of these can be used without influencing the effect of the invention. Methionine is frequently used as an excipient for pharmaceutical products, and an L form described in the Japanese Pharmacopoeia (the 16th Edition) is preferable. While the content of methionine per volume in the aqueous liquid composition of the present invention is not particularly defined, it is preferably 1-300 mM.

The "alpha hydroxy acid", "dicarboxylic acid" and "methionine" can each stabilize the aqueous liquid composition of the present invention even by a single use thereof. Further stability can be expected by using "methionine" in combination with "alpha hydroxy acid" and/or "dicarboxylic acid". In this case, an acid to be combined with "methionine" is preferably glycolic acid, lactic acid, malic acid, tartaric acid, succinic acid, maleic acid or fumaric acid, more preferably malic acid or tartaric acid, most preferably tartaric acid.

While the aqueous liquid composition of the present invention has pH 3-6, when a desired pH is not achieved during production, a pH adjuster is generally used to adjust pH. From the aspect of stability, preferable pH is 3-6, more preferable pH is 4-5. When pH is less than 3 or exceeds 6, analogues such as an oxidized form of a methionine residue in the peptide of the present invention and the like tend to increase during production or storage. As a result, the content of the peptide of the present invention in the aqueous liquid composition may decrease unpreferably.

A pH adjuster is selected as appropriate from the pH adjusters generally used for pharmaceutical preparations and used. Specifically, hydrochloric acid, phosphoric acid, sodium hydroxide, potassium hydroxide, sodium hydrogen phosphate, sodium dihydrogen phosphate, potassium dihydrogen phosphate, trisodium phosphate and the like can be mentioned.

In addition, the aqueous liquid composition of the present invention may appropriately comprise, besides the above-mentioned excipients, excipients generally used for pharmaceutical preparations such as stabilizer, solubilizer, buffering agent, isotonic agent, solubilizing agent and the like, as long as the effect of the invention is not affected.

The aqueous liquid composition of the present invention can be produced by a method generally used for the production of pharmaceutical products and the like. For example, water for injection is added into a suitable container under an environment maintained at a constant temperature of 5-25° C., and a peptide and an excipient which are weighed in advance are added thereto while gently stirring the mixture. Then, the mixture is finally adjusted to have a desired pH. The mixture is sterilized by filtration and the like, and filled in a container such as a glass vial and the like, which is sealed with a rubber stopper and the like.

While the preparation method of a cancer vaccine using the aqueous liquid composition of the present invention is not particularly limited, for example, a preparation method of a cancer vaccine by mixing with an appropriate adjuvant; a preparation method of a cancer vaccine by mixing with an appropriate adjuvant in advance, and freeze-drying the mixture and the like; a preparation method of a cancer vaccine by mixing the aqueous liquid composition of the present invention with various adjuvants when in use and the like can be mentioned. Examples of the adjuvant include Freund's adjuvant; mineral gel such as aluminum hydroxide; surface active substance such as lysolecithin, pluronic polyol, polyanion, peptide, oil emulsion, keyhole limpet hemocyanin and dinitrophenol; human adjuvant such as BCG (Bacille de Calmette et Guérin) and *Corynebacterium parvum* and the like.

A cancer vaccine prepared using the aqueous liquid composition of the present invention can be used for the prevention or treatment of cancer associated with an increase in the expression level of WT1 gene, for example, hematological cancer such as leukemia, myelodysplastic syndrome, multiple myeloma, malignant lymphoma and the like, and solid tumor such as gastric cancer, colorectal cancer, lung cancer, breast cancer, germ cell cancer, liver cancer, skin cancer, urinary bladder cancer, prostate cancer, uterine cancer, cervical cancer, ovarian cancer and the like.

Since the aqueous liquid composition of the present invention can stably maintain a cancer antigen peptide, which is the active ingredient, various administration forms can be selected. Specifically, oral, transnasal, pulmonary, transdermal, intradermal, subcutaneous, intramuscular, intravenous or intraperitoneal administration and the like can be mentioned, and a cancer vaccine can be prepared by the above-mentioned method according to the object of use. Generally, as an administration route preferable for immunostimulation with a cancer vaccine, parenteral administration is known and, for example, intraperitoneal administration, subcutaneous administration, intradermal administration, intramuscular administration, intravenous administration, as well as transnasal administration, transdermal administration and the like can be mentioned. Of these, administration by injection such as subcutaneous administration, intradermal administration, intraperitoneal administration, intramuscular administration and the like can be preferably mentioned.

EXAMPLES

The present invention is explained in more detail in the following by referring to Examples, Comparative Examples, Experimental Examples and the like, which are not to be construed as limitative. In the following Examples and the like, "%" means "wt %" unless otherwise specified.

The "glycolic acid (crystal) (manufactured by Nacalai Tesque)" was used as glycolic acid, "lactic acid (manufactured by Nacalai Tesque)" was used as lactic acid, "DL-malic acid (manufactured by Nacalai Tesque)" was used as malic acid, "L(+)-Tartaric acid, powder (manufactured by Merck)" was used as tartaric acid, and "citric acid monohydrate (manufactured by Nacalai Tesque)" was used as citric acid. The "malonic acid (manufactured by Nacalai Tesque)" was used as malonic acid, "succinic acid (manufactured by Nacalai Tesque)" was used as succinic acid, "glutaric acid (manufactured by Nacalai Tesque)" was used as glutaric acid, "maleic acid (manufactured by Nacalai Tesque)" was used as maleic acid, and "L-methionine (manufactured by Kyowa Hakko Bio Co., Ltd.)" was used as methionine. For adjusting pH, "1 mol/l-hydrochloric acid (manufactured by Nacalai Tesque)" was used as hydrochloric acid, and "1 mol/l-sodium hydroxide solution (manufactured by Nacalai Tesque)" was used as sodium hydroxide.

In Comparative Examples, "sodium dihydrogen phosphate dehydrate (manufactured by Nacalai Tesque)" was used as sodium dihydrogen phosphate, "sodium acetate trihydrate (manufactured by Nacalai Tesque)" was used as sodium acetate, "sodium thioglycolate (manufactured by Nacalai Tesque)" was used as sodium thioglycolate, "sodium pyrosulfite (manufactured by Nacalai Tesque)" was used as sodium pyrosulfite, and "L(+)-ascorbic acid (manufactured by Nacalai Tesque)" was used as ascorbic acid.

"L-α-alanine (manufactured by Nacalai Tesque)" was used as alanine, "glycine (manufactured by Nacalai Tesque)" was used as glycine, and "L-arginine hydrochloride (manufactured by Nacalai Tesque)" was used as arginine.

"IFA (manufactured by Wako Pure Chemical Industries, Ltd.)" was used as Incomplete Freund's adjuvant, "NOFABLE EO-85S (manufactured by NOF Corp.)" was used as ethyl oleate, "NOFABLE SO-991 (manufactured by NOF Corp.)" was used as sorbitan monooleate, "NIKKOL HCO-10 (manufactured by Nikko Chemicals)" was used as polyoxyethylene hydrogenated castor oil 10, and "the Japanese Pharmacopoeia concentrated glycerin (manufactured by NOF Corp.)" was used as concentrated glycerin. "NIKKOL ODM-100 (manufactured by Nikko Chemicals)" was used as octyldodecyl myristate, "NOFABLE GO-991 (manufactured by NOF Corp.)" was used as glycerol monooleate, and "NIKKOL HCO-20 (manufactured by Nikko Chemicals)" was used as polyoxyethylene hydrogenated castor oil 20.

[Preparation of Aqueous Liquid Composition]

Example 1

A peptide shown by SEQ ID NO: 1 (RMFPNAPYL) (hereinafter peptide (1)), which is peptide (A), as peptide and glycolic acid, which is excipient (C), as excipient were dissolved in water for injection in the amounts described in Table 1, and adjusted to pH 4.5 with hydrochloric acid and/or sodium hydroxide. The mixture was filtered through a 0.2 μm sterilized filter, filled in a glass vial by 1 mL, and the vial was sealed with a butyl rubber stopper, whereby aqueous liquid composition 1 was obtained.

Examples 2-38

In the same manner as in Example 1, peptide (1) which is peptide (A), and alpha hydroxy acid, dicarboxylic acid and/or methionine as excipients (C), (D) and/or (E) were prepared in the amounts described in Tables 1-9, filled in vials, and the vials were sealed with a butyl rubber stopper, whereby aqueous liquid compositions 2-38 were obtained.

Comparative Examples 1-23

In the same manner as in Example 1, the amounts described in Tables 10-14 were prepared, filled in vials, and the vials were sealed with a butyl rubber stopper, whereby aqueous liquid compositions 39-61 were obtained.

TABLE 1

| | Example | | | | |
|---|---|---|---|---|---|
| | 1 | 2 | 3 | 4 | 5 |
| | aqueous liquid composition No. | | | | |
| | 1 | 2 | 3 | 4 | 5 |
| peptide (1) [mg/mL] | 0.2 | 0.2 | 0.2 | 0.2 | 0.2 |
| glycolic acid [mM] | 10 | — | — | — | — |
| lactic acid [mM] | — | 10 | — | — | — |
| malic acid [mM] | — | — | 10 | — | — |
| tartaric acid [mM] | — | — | — | 10 | — |
| citric acid [mM] | — | — | — | — | 10 |
| hydrochloric acid/ sodium hydroxide | q.s. | q.s. | q.s. | q.s. | q.s. |
| pH | 4.5 | 4.5 | 4.6 | 4.6 | 4.6 |

TABLE 2

| | Example | | | |
|---|---|---|---|---|
| | 6 | 7 | 8 | 9 |
| | aqueous liquid composition No. | | | |
| | 6 | 7 | 8 | 9 |
| peptide (1) [mg/mL] | 0.2 | 0.2 | 0.2 | 0.2 |
| malonic acid [mM] | 25 | — | — | — |
| succinic acid [mM] | — | 25 | — | — |
| glutaric acid [mM] | — | — | 25 | — |
| maleic acid [mM] | — | — | — | 25 |
| hydrochloric acid/ sodium hydroxide | q.s. | q.s. | q.s. | q.s. |
| pH | 4.5 | 4.5 | 4.5 | 4.5 |

TABLE 3

| | Example | | | |
|---|---|---|---|---|
| | 10 | 11 | 12 | 13 |
| | aqueous liquid composition No. | | | |
| | 10 | 11 | 12 | 13 |
| peptide (1) [mg/mL] | 0.2 | 0.2 | 0.2 | 0.2 |
| malic acid [mM] | 1 | 25 | 50 | 100 |
| hydrochloric acid/ sodium hydroxide | q.s. | q.s. | q.s. | q.s. |
| pH | 4.6 | 4.5 | 4.5 | 4.5 |

TABLE 4

| | Example | | |
|---|---|---|---|
| | 14 | 15 | 16 |
| | aqueous liquid composition No. | | |
| | 14 | 15 | 16 |
| peptide (1) [mg/mL] | 0.2 | 0.2 | 0.2 |
| succinic acid [mM] | 10 | 50 | 100 |
| hydrochloric acid/ sodium hydroxide | q.s. | q.s. | q.s. |
| pH | 4.5 | 4.5 | 4.5 |

TABLE 5

| | Example | | | | |
|---|---|---|---|---|---|
| | 17 | 18 | 19 | 20 | 21 |
| | aqueous liquid composition No. | | | | |
| | 17 | 18 | 19 | 20 | 21 |
| peptide (1) [mg/mL] | 0.2 | 0.2 | 0.2 | 0.2 | 0.2 |
| methionine [mM] | 1 | 50 | 100 | 200 | 300 |
| hydrochloric acid/ sodium hydroxide | q.s. | q.s. | q.s. | q.s. | q.s. |
| pH | 4.5 | 4.5 | 4.5 | 4.5 | 4.5 |

TABLE 6

| | Example | | | | |
|---|---|---|---|---|---|
| | 22 | 23 | 24 | 25 | 26 |
| aqueous liquid composition No. | 22 | 23 | 24 | 25 | 26 |
| peptide (1) [mg/mL] | 0.2 | 0.2 | 0.2 | 0.2 | 0.2 |
| tartaric acid [mM] | 1 | 1 | — | — | 10 |
| glutaric acid [mM] | — | — | 50 | — | — |
| succinic acid [mM] | — | — | — | 50 | 25 |
| methionine [mM] | — | 1 | 1 | 1 | 1 |
| hydrochloric acid/sodium hydroxide | q.s. | q.s. | q.s. | q.s. | q.s. |
| pH | 4.5 | 4.5 | 4.5 | 4.5 | 4.5 |

TABLE 7

| | Example | | | | | | |
|---|---|---|---|---|---|---|---|
| | 27 | 28 | 29 | 30 | 31 | 32 | 33 |
| aqueous liquid composition No. | 27 | 28 | 29 | 30 | 31 | 32 | 33 |
| peptide (1) [mg/mL] | 0.2 | 1.7 | 2 | 5 | 16.7 | 50 | 100 |
| tartaric acid [mM] | 10 | 10 | 10 | 10 | 10 | 10 | 10 |
| methionine [mM] | 200 | 200 | 200 | 200 | 200 | 200 | 200 |
| hydrochloric acid/sodium hydroxide | q.s. | q.s. | q.s. | q.s. | q.s. | q.s. | q.s. |
| pH | 4.5 | 4.5 | 4.5 | 4.5 | 4.5 | 4.5 | 4.5 |

TABLE 8

| | Example | |
|---|---|---|
| | 34 | 35 |
| aqueous liquid composition No. | 34 | 35 |
| peptide (1) [mg/mL] | 0.01 | 50 |
| malic acid [mM] | 1 | — |
| tartaric acid [mM] | — | 10 |
| hydrochloric acid/sodium hydroxide | q.s. | q.s. |
| pH | 4.5 | 4.5 |

TABLE 9

| | Example | | |
|---|---|---|---|
| | 36 | 37 | 38 |
| aqueous liquid composition No. | 36 | 37 | 38 |
| peptide (1) [mg/mL] | 20 | 20 | 20 |
| tartaric acid [mM] | 10 | — | 10 |
| methionine [mM] | 50 | 200 | 200 |
| hydrochloric acid/sodium hydroxide | q.s. | q.s. | q.s. |
| pH | 4.5 | 4.5 | 4.5 |

TABLE 10

| | Comparative Example | | | | | |
|---|---|---|---|---|---|---|
| | 1 | 2 | 3 | 4 | 5 | 6 |
| aqueous liquid composition No. | 39 | 40 | 41 | 42 | 43 | 44 |
| peptide (1) [mg/mL] | 0.2 | 0.2 | 0.2 | 0.2 | 0.2 | 0.2 |
| sodium dihydrogen phosphate [mM] | — | 1 | — | — | — | — |
| sodium acetate [mM] | — | — | 1 | — | — | — |
| alanine [mM] | — | — | — | 1 | — | — |
| glycine [mM] | — | — | — | — | 1 | — |
| arginine [mM] | — | — | — | — | — | 1 |
| hydrochloric acid/sodium hydroxide | q.s. | q.s. | q.s. | q.s. | q.s. | q.s. |
| pH | 4.5 | 4.5 | 4.5 | 4.5 | 4.5 | 4.5 |

TABLE 11

| | Comparative Example | | | | |
|---|---|---|---|---|---|
| | 7 | 8 | 9 | 10 | 11 |
| aqueous liquid composition No. | 45 | 46 | 47 | 48 | 49 |
| peptide (1) [mg/mL] | 0.2 | 0.2 | 0.2 | 0.2 | 0.2 |
| sodium dihydrogen phosphate [mM] | 50 | — | — | — | — |
| sodium acetate [mM] | — | 50 | — | — | — |
| alanine [mM] | — | — | 50 | — | — |
| glycine [mM] | — | — | — | 50 | — |
| arginine [mM] | — | — | — | — | 50 |
| hydrochloric acid/sodium hydroxide | q.s. | q.s. | q.s. | q.s. | q.s. |
| pH | 4.5 | 4.5 | 4.5 | 4.5 | 4.6 |

TABLE 12

| | Comparative Example | | |
|---|---|---|---|
| | 12 | 13 | 14 |
| aqueous liquid composition No. | 50 | 51 | 52 |
| peptide (1) [mg/mL] | 0.2 | 0.2 | 0.2 |
| alanine [mM] | 200 | — | — |
| glycine [mM] | — | 200 | — |
| arginine [mM] | — | — | 200 |
| hydrochloric acid/sodium hydroxide | q.s. | q.s. | q.s. |
| pH | 4.5 | 4.5 | 4.5 |

TABLE 13

| | Comparative Example | | | |
|---|---|---|---|---|
| | 15 | 16 | 17 | 18 |
| aqueous liquid composition No. | 53 | 54 | 55 | 56 |
| peptide (1) [mg/mL] | 0.01 | 0.01 | 50 | 50 |
| sodium dihydrogen phosphate [mM] | — | 1 | — | 10 |
| hydrochloric acid/sodium hydroxide | q.s. | q.s. | q.s. | q.s. |
| pH | 4.5 | 4.5 | 4.5 | 4.5 |

TABLE 14

| | Comparative Example | | | | |
|---|---|---|---|---|---|
| | 19 | 20 | 21 | 22 | 23 |
| | aqueous liquid composition No. | | | | |
| | 57 | 58 | 59 | 60 | 61 |
| peptide (1) [mg/mL] | 20 | 20 | 20 | 20 | 20 |
| ascorbic acid [%] | — | — | 0.1 | — | — |
| sodium thioglycolate [%] | — | — | — | 0.1 | — |
| sodium pyrosulfite [%] | — | — | — | — | 0.1 |
| hydrochloric acid/sodium hydroxide | q.s. | q.s. | q.s. | q.s. | q.s. |
| pH | 4.5 | 4.6 | 4.7 | 4.7 | 4.6 |

[Experimental Example 1] Stability Evaluation (1)

The prepared aqueous liquid compositions were stored in an incubator at 60° C. for 2 weeks. Then, the content of oxidized peptide, which was the peptide resulting from oxidation of a methionine residue contained in peptide (1), was measured based on the following method.

Using a C18 reversed-phase column (4.6 mm×150 mm, 3.5 μm), the content of oxidized peptide was measured by the reversed-phase system high performance liquid chromatography method using pure water, acetonitrile, methanol, and trifluoroacetic acid for the mobile phase. As peptide (1), an amount equivalent to 10 μg was injected, and spectroscopic detection at a wavelength of 220 nm was performed. Using the peak area measured by this method, the content of oxidized peptide (%) was calculated by the following formula.

Content of oxidized peptide (%)=peak area of oxidized peptide/total peak area of peptide comprising related substances×100

Among the aqueous liquid compositions obtained in Examples and Comparative Examples, Examples 1-22 described in Tables 1-6, and Comparative Examples 1-14 described in Tables 10-12 were stored at 60° C. for 2 weeks. The content of oxidized peptide after storage are shown in Tables 15 and 16. The inhibition ratio of oxidized product in the Tables was calculated by the following formula.

Inhibition ratio of oxidized product (%)={(content of oxidized peptide in control sample (Comparative Example 1))−(content of oxidized peptide in Example or Comparative Example in Table 15 or Table 16)}×100/(content of oxidized peptide in control sample (Comparative Example 1))

A higher numerical value of inhibition ratio of oxidized product means a higher inhibition effect for oxidation and a high stabilizing effect of the excipient for peptide (1).

TABLE 15

| | aqueous liquid composition No. | peptide concentration | excipient | 60° C., 2 weeks later | |
|---|---|---|---|---|---|
| | | | | content of oxidized peptide | inhibition ratio of oxidized product |
| Comparative Example 1 (control) | 39 | 0.2 mg/mL | None | 1.39% | — |
| Example 1 | 1 | 0.2 mg/mL | 10 mM glycolic acid | 0.56% | 60% |
| Example 2 | 2 | 0.2 mg/mL | 10 mM lactic acid | 0.62% | 55% |
| Example 3 | 3 | 0.2 mg/mL | 10 mM malic acid | 0.41% | 71% |
| Example 4 | 4 | 0.2 mg/mL | 10 mM tartaric acid | 0.64% | 54% |
| Example 5 | 5 | 0.2 mg/mL | 10 mM citric acid | 1.13% | 19% |
| Example 6 | 6 | 0.2 mg/mL | 25 mM malonic acid | 1.03% | 26% |
| Example 7 | 7 | 0.2 mg/mL | 25 mM succinic acid | 0.67% | 52% |
| Example 8 | 8 | 0.2 mg/mL | 25 mM glutaric acid | 1.00% | 28% |
| Example 9 | 9 | 0.2 mg/mL | 25 mM maleic acid | 0.17% | 88% |
| Example 10 | 10 | 0.2 mg/mL | 1 mM malic acid | 0.45% | 68% |
| Example 11 | 11 | 0.2 mg/mL | 25 mM malic acid | 0.42% | 70% |
| Example 12 | 12 | 0.2 mg/mL | 50 mM malic acid | 0.55% | 60% |
| Example 13 | 13 | 0.2 mg/mL | 100 mM malic acid | 0.70% | 50% |
| Example 14 | 14 | 0.2 mg/mL | 10 mM succinic acid | 0.96% | 31% |
| Example 15 | 15 | 0.2 mg/mL | 50 mM succinic acid | 0.37% | 73% |
| Example 16 | 16 | 0.2 mg/mL | 100 mM succinic acid | 0.33% | 76% |
| Example 17 | 17 | 0.2 mg/mL | 1 mM methionine | 0.39% | 72% |
| Example 18 | 18 | 0.2 mg/mL | 50 mM methionine | 0.13% | 91% |
| Example 19 | 19 | 0.2 mg/mL | 100 mM methionine | 0.13% | 91% |
| Example 20 | 20 | 0.2 mg/mL | 200 mM methionine | 0.14% | 90% |
| Example 21 | 21 | 0.2 mg/mL | 300 mM methionine | 0.15% | 89% |
| Example 22 | 22 | 0.2 mg/mL | 1 mM tartaric acid | 0.49% | 65% |

TABLE 16

| | aqueous liquid composition No. | peptide concentration | excipient | 60° C., 2 weeks later | |
|---|---|---|---|---|---|
| | | | | content of oxidized peptide | inhibition ratio of oxidized product |
| Comparative Example 1 (control) | 39 | 0.2 mg/mL | none | 1.39% | — |
| Comparative Example 2 | 40 | 0.2 mg/mL | 1 mM sodium dihydrogen phosphate | 1.43% | −3% |
| Comparative Example 3 | 41 | 0.2 mg/mL | 1 mM sodium acetate | 1.43% | −3% |
| Comparative Example 4 | 42 | 0.2 mg/mL | 1 mM alanine | 1.30% | 6% |
| Comparative Example 5 | 43 | 0.2 mg/mL | 1 mM glycine | 1.27% | 9% |
| Comparative Example 6 | 44 | 0.2 mg/mL | 1 mM arginine | 1.32% | 5% |

TABLE 16-continued

| aqueous liquid composition No. | peptide con-centration | excipient | 60° C., 2 weeks later content of oxidized peptide | 60° C., 2 weeks later inhibition ratio of oxidized product |
|---|---|---|---|---|
| Comparative Example 7 | 45 | 0.2 mg/mL | 50 mM sodium dihydrogen phosphate | 1.76% | -27% |
| Comparative Example 8 | 46 | 0.2 mg/mL | 50 mM sodium acetate | 1.31% | 6% |
| Comparative Example 9 | 47 | 0.2 mg/mL | 50 mM alanine | 1.33% | 4% |
| Comparative Example 10 | 48 | 0.2 mg/mL | 50 mM glycine | 1.83% | -32% |
| Comparative Example 11 | 49 | 0.2 mg/mL | 50 mM arginine | 1.28% | 8% |
| Comparative Example 12 | 50 | 0.2 mg/mL | 200 mM alanine | 1.30% | 6% |
| Comparative Example 13 | 51 | 0.2 mg/mL | 200 mM glycine | 2.80% | -101% |
| Comparative Example 14 | 52 | 0.2 mg/mL | 200 mM arginine | 1.94% | -40% |

As Comparative Example, the inhibition effect for oxidation of peptide (1) was evaluated by adding general acid or amino acids as a excipient. In the result, the excipient has almost no inhibition effect for oxidation (less than 10%) or an increase in the content of oxidized peptide. In contrast, when the excipient in the present invention was added, an inhibition effect for oxidation was always found. According to Table 15, it was confirmed that the inhibition effect for oxidation is scarcely influenced by the content per volume of the excipient of the present invention.

[Experimental Example 2] Stability Evaluation (2)

The prepared aqueous liquid compositions were stored in an incubator at 60° C. for 2 weeks. Then, the content of oxidized peptide, which was the peptide resulting from oxidation of a methionine residue, was measured in the same manner as in the stability evaluation (1).

Among the aqueous liquid compositions obtained in Examples and Comparative Examples, Examples 23-27 described in Tables 6 and 7, and Comparative Example 1 described in Table 10 were stored at 60° C. for 2 weeks. The contents of oxidized peptide after storage are shown in Table 17. The inhibition ratio of oxidized product in the Table was calculated in the same manner as in the stability evaluation (1).

TABLE 17

| aqueous liquid composition No. | peptide con-centration | excipient | 60° C., 2 weeks later content of oxidized peptide | 60° C., 2 weeks later inhibition ratio of oxidized product |
|---|---|---|---|---|
| Comparative Example 1 (control) | 39 | 0.2 mg/mL | None | 1.39% | — |
| Example 23 | 23 | 0.2 mg/mL | 1 mM tartaric acid + 1 mM methionine | 0.31% | 78% |
| Example 24 | 24 | 0.2 mg/mL | 50 mM glutaric acid + 1 mM methionine | 0.29% | 79% |
| Example 25 | 25 | 0.2 mg/mL | 50 mM succinic acid + 1 mM methionine | 0.21% | 85% |
| Example 26 | 26 | 0.2 mg/mL | 10 mM tartaric acid + 25 mM succinic acid + 1 mM methionine | 0.28% | 80% |
| Example 27 | 27 | 0.2 mg/mL | 10 mM tartaric acid + 200 mM methionine | 0.13% | 91% |

According to Table 17, it could be confirmed that a higher inhibition effect for oxidation as compared to the control was obtained by using a combination of two or more kinds of the excipient in the present invention.

[Experimental Example 3] Stability Evaluation (3)

The prepared aqueous liquid compositions were stored in an incubator at 60° C. for 2 weeks. Then, the content of oxidized peptide, which was the peptide resulting from oxidation of a methionine residue, was measured in the same manner as in the stability evaluation (1).

Among the aqueous liquid compositions obtained in Examples and Comparative Examples, Comparative Example 19 described in Table 14, and Example 37 described in Table 9 were stored at 60° C. for 2 weeks. The contents of oxidized peptide after storage are shown in Table 18. The inhibition ratio of oxidized product in the Table was calculated by the following formula.

Inhibition ratio of oxidized product (%)={(content of oxidized peptide in control sample (Comparative Example 19))−(content of oxidized peptide in Example 37 in Table 18)}×100/(content of oxidized peptide in control sample (Comparative Example 19))

A higher numerical value of inhibition ratio of oxidized product means a higher inhibition effect for oxidation, and a high stabilizing effect of the excipient for peptide (1).

TABLE 18

| aqueous liquid composition No. | peptide con-centration | excipient | 60° C., 2 weeks later content of oxidized peptide | 60° C., 2 weeks later inhibition ratio of oxidized product |
|---|---|---|---|---|
| Comparative Example 19 (control) | 57 | 20 mg/mL | None | 1.07% | — |
| Example 37 | 37 | 20 mg/mL | 200 mM methionine | 0.23% | 79% |

According to Table 15 and Table 18, it could be confirmed that the excipient in the present invention shows an inhibition effect for oxidation regardless of the peptide concentration of the aqueous liquid composition.

[Experimental Example 4] Stability Evaluation (4)

The prepared aqueous liquid compositions were stored in an incubator at 40° C. for 4 weeks. Then, the content of oxidized peptide, which was the peptide resulting from oxidation of a methionine residue, was measured in the same manner as in the stability evaluation (1). A C18 reversed-phase column (4.6 mm×150 mm, 5 μm) was used, and pure water, acetonitrile, and trifluoroacetic acid were used for the mobile phase.

Among the aqueous liquid compositions obtained in Comparative Examples, Comparative Examples 20-23 described in Table 14 were stored at 40° C. for 4 weeks. The contents of oxidized peptide after storage are shown in Table 19. The inhibition ratio of oxidized product in the Table was calculated by the following formula.

Inhibition ratio (%)={(content of oxidized peptide in control sample (Comparative Example 20))−(content of oxidized peptide in Comparative Example in Table 19)}×100/(content of oxidized peptide in control sample (Comparative Example 20))

A higher numerical value of inhibition ratio of oxidized product means a higher inhibition effect for oxidation, and a high stabilizing effect of the excipient for peptide (1).

TABLE 19

| | aqueous liquid composition No. | peptide concentration | excipient | 40° C., 4 weeks later | |
|---|---|---|---|---|---|
| | | | | content of oxidized peptide | inhibition ratio of oxidized product |
| Comparative Example 20 (control) | 58 | 20 mg/mL | None | 0.47% | — |
| Comparative Example 21 | 59 | 20 mg/mL | 0.1% ascorbic acid | 3.11% | −562% |
| Comparative Example 22 | 60 | 20 mg/mL | 0.1% sodium thioglycolate | 0.73% | −55% |
| Comparative Example 23 | 61 | 20 mg/mL | 0.1% sodium pyrosulfite | 8.57% | −1723% |

As shown in Table 19, it was confirmed that addition of ascorbic acid, sodium thioglycolate or sodium pyrosulfite, which are antioxidants generally used for liquid formulations, instabilizes peptide (1) as compared to the control and increase an oxidized product.

[Experimental Example 5] Confirmation of Specific CTL-Inducing Activity

The aqueous liquid compositions 36, 37 and 38 were mixed with adjuvants to give cancer vaccine compositions.
1) Preparation of Cancer Vaccine Compositions a1, a2

As adjuvant a, incomplete Freund's adjuvant was used. Aqueous liquid composition 36 was diluted 1.7-fold with peptide-free 10 mM tartaric acid+50 mM methionine solution. 450 μL of foregoing mixture was taken in a glass syringe (Top Corp.), and the syringe was connected with a joint to another glass syringe containing 450 μL of adjuvant a. The inner cylinder of the both glass syringes were alternately pressed thereinto 30 times or more to emulsify the solution, whereby cancer vaccine composition a1 was obtained.

Similarly, aqueous liquid composition 38 was diluted 1.7-fold with peptide-free 10 mM tartaric acid+200 mM methionine solution, and processed using adjuvant a under similar conditions to give cancer vaccine composition a2.
2) Preparation of Cancer Vaccine Compositions b1, b2

Ethyl oleate (96.5 g), sorbitan monooleate (17.5 g), polyoxyethylene hydrogenated castor oil 10 (4.5 g), concentrated glycerin (1.5 g), and 25 mM aqueous sodium dihydrogen phosphate solution (20.0 g) were taken in a 300 mL glass tall beaker in advance. Then, the mixture was stirred using CLEAMIX CLM-1.5 (M Technique Co., Ltd.) at 10000 rpm for 5 min to give adjuvant b.

Then, 400 μL of aqueous liquid composition 37, and 930 μL of adjuvant b were mixed by a test tube mixer (touch mixer MT-51, Yamato Scientific Co., Ltd.) to give cancer vaccine composition b1.

Also, aqueous liquid composition 38 and adjuvant b were processed under similar conditions to give cancer vaccine composition b2.
3) Preparation of Cancer Vaccine Compositions c1, c2

Ethyl oleate (49.0 g), octyldodecyl myristate (49.0 g), sorbitan monooleate (7.0 g), glycerol monooleate (9.8 g), polyoxyethylene hydrogenated castor oil 20 (1.4 g), concentrated glycerin (1.4 g), and 25 mM aqueous sodium dihydrogen phosphate solution (22.4 g) were taken in a 300 mL glass tall beaker in advance. Then, the mixture was stirred using CLEAMIX CLM-1.5 (M Technique Co., Ltd.) at 10000 rpm for 5 min to give adjuvant c.

Then, 400 μL of aqueous liquid composition 36, and 930 μL of adjuvant c were mixed by a test tube mixer (touch mixer MT-51, Yamato Scientific Co., Ltd.) to give cancer vaccine composition c1.

Also, aqueous liquid composition 38 and adjuvant c were processed under similar conditions to give cancer vaccine composition c2.
4) CTL-Inducing Activity Evaluation The specific CTL-inducing ability of 6 kinds of cancer vaccine compositions (a1-c2) prepared in the above-mentioned 1) to 3) was evaluated using HLA-A*0201 transgenic mouse (Eur. J. Immunol.: 34, 3060, 2004).

100 μL of each cancer vaccine composition (600 μg as peptide dose) was intradermally administered to HLA-A*0201 transgenic mouse from the base of the tail. Three mice were used for each group. The spleen was isolated 7 days after the administration, and the splenocytes were prepared. A part of the splenocytes was pulsed with 100 μmol/L peptide (1) for 1 hr. The pulsing means that peptide (1) was added to splenocytes to allow for binding of antigen peptide to HLA on the cell surface. Splenocytes without pulsing with peptide (1) and the above-mentioned splenocytes pulsed with peptide were mixed, plated on a 24 well plate at $7.8 \times 10^6$ cells/well, and cultured. As the culture medium, RPMI1640 medium supplemented with 10% FCS, 10 mM HEPES, 20 mM L-glutamine, 1 mM sodium pyruvate, 1 mM MEM non-essential amino acid, 1% MEM vitamin, and 55 μM 2-mercaptoethanol was used, and the cells were cultured for 5 days. The administered peptide-specific CTL activity of the cultured splenocytes was measured by $^{51}$Cr release assay (J. Immunol.: 159, 4753, 1997). For stable expression of HLA-A*0201 and H-2D$^b$ chimeric MHC class I molecule, cell line EL4-HHD cell prepared in the Institut Pasteur by gene transfer into mouse lymphoma-derived cell line (J. Exp. Med.: 185, 2043, 1997) was used. The target cells were $^{51}$Cr-labeled with 3.7 MBq/$5 \times 10^5$ cells for 1 hr, the aforementioned peptide was added to 167 μmol/L and the cells was further pulsed for 1 hr. In addition, the target cells not pulsed with the aforementioned peptide (non-pulsed) were $^{51}$Cr-labeled for 2 hr to give control target cells. The labeled target cells and the splenocytes prepared earlier were mixed at a ratio of 1:20, cultured for 4 hr, and the CTL-inducing activity (namely, cytotoxicity) was determined from the ratio of the injured target cells. The results are shown in FIG. 1. The cytotoxicity is shown by the mean value of 3 mice for each administration group.

As shown in FIG. 1, the group administered with a cancer vaccine composition prepared using the aqueous liquid composition of the present invention showed high cytotoxicity against the target cells pulsed with the aforementioned peptide, but showed low cytotoxicity against the control target cells not pulsed with the aforementioned peptide, which has clarified induction of peptide-specific CTL. The results show that the aqueous liquid composition of the present invention combined with various adjuvants activates induction of CTL specific to cancer antigen.

[Preparation of Aqueous Liquid Composition]

[Examples 39-44], [Comparative Example 24]

Peptide (1), which is peptide (A), as peptide, tartaric acid, which is excipient (C), as excipient and methionine as excipient (E) were dissolved in water for injection in the amounts described in Table 20, and adjusted to the pH described in Table 20 with hydrochloric acid or/and sodium hydroxide. The mixture was filtered through a 0.2 μm sterilized filter, filled in a glass vial by 1 mL, and the vial was sealed with a butyl rubber stopper, whereby aqueous liquid compositions 62-68 were obtained.

TABLE 20

|  | Example | | | | | | Comparative Example |
|---|---|---|---|---|---|---|---|
|  | 39 | 40 | 41 | 42 | 43 | 44 | 24 |
|  | aqueous liquid composition No. | | | | | | |
|  | 62 | 63 | 64 | 65 | 66 | 67 | 68 |
| peptide (1) [mg/mL] | 50 | 50 | 50 | 50 | 50 | 50 | 50 |
| tartaric acid [mM] | 10 | 10 | 10 | 10 | 10 | 10 | 10 |
| methionine [mM] | 200 | 200 | 200 | 200 | 200 | 200 | 200 |
| hydrochloric acid/sodium hydroxide | q.s. | q.s. | q.s. | q.s. | q.s. | q.s | q.s. |
| pH | 3.0 | 4.0 | 4.5 | 5.0 | 5.5 | 6.0 | 7.1 |

[Experimental Example 6] Stability Evaluation (5)

The prepared aqueous liquid compositions were stored in an incubator at 40° C. for 1 month. Then, the content of peptide (1) (hereinafter peptide content) was measured based on the following method.

Using a C18 reversed-phase column (4.6 mm×150 mm, 3.5 μm), the peptide content was measured by the reversed-phase system high performance liquid chromatography method using pure water, acetonitrile, methanol, and trifluoroacetic acid for the mobile phase. As peptide (1), an amount equivalent to 10 μg was injected, and spectroscopic detection at a wavelength of 220 nm was performed. Using the peak area measured by this method, the peptide content (%) was calculated by the following formula.

Peptide content (%)=peak area of peptide (1)/total peak area of peptide containing related substances×100

The peptide content before storage (initial) (%) was measured in the same manner, and the residual ratio of peptide (%) was calculated by the following formula.

Residual ratio of peptide (%)=peptide content after storage (%)/peptide content (initial)(%)×100

Among the aqueous liquid compositions obtained in Examples and Comparative Examples, Examples 39-44 described in Table 20, and Comparative Example 24 described in Table 20 were stored at 40° C. for 1 month. The residual ratios of peptide (%) are shown in Table 21.

TABLE 21

|  | aqueous liquid composition No. | pH | 40° C., 1 month later residual ratio of peptide |
|---|---|---|---|
| Example 39 | 62 | 3.0 | 97.4% |
| Example 40 | 63 | 4.0 | 99.0% |
| Example 41 | 64 | 4.5 | 99.2% |
| Example 42 | 65 | 5.0 | 99.0% |
| Example 43 | 66 | 5.5 | 98.5% |
| Example 44 | 67 | 6.0 | 97.4% |
| Comparative Example 24 | 68 | 7.1 | 92.5% |

As shown in Table 21, aqueous liquid compositions with high stability showing the residual ratio of not less than 97% were obtained when the pH was within the range of 3-6. On the other hand, the residual ratio of peptide decreased when the pH was 7.1.

[Experimental Example 7] Stability Evaluation (6)

The prepared aqueous liquid compositions were stored in an incubator at 40° C. for 4 weeks. The content of oxidized peptide after storage was measured in the same manner as in the stability evaluation (1).

Among the aqueous liquid compositions obtained in Examples and Comparative Examples, Example 34 described in Table 8, and Comparative Examples 15, 16 described in Table 13 were stored at 40° C. for 4 weeks. The contents of oxidized peptide after storage are shown in Table 22. The inhibition ratio of oxidized product in the Table was calculated by the following formula.

Inhibition ratio of oxidized product (%)={(content of oxidized peptide in control sample (Comparative Example 15))−(content of oxidized peptide in Example 34 in Table 8 or Comparative Example 16 in Table 13)}×100/(content of oxidized peptide in control sample (Comparative Example 15))

A higher numerical value of inhibition ratio of oxidized product means a higher inhibition effect for oxidation, and a high stabilizing effect of the excipient for peptide (1).

TABLE 22

|  | aqueous liquid composition No. | peptide concentration | excipient | 40° C., 4 weeks later | |
|---|---|---|---|---|---|
|  |  |  |  | content of oxidized peptide | inhibition ratio of oxidized product |
| Comparative Example 15 (control) | 53 | 0.01 mg/mL | None | 2.37% | — |

TABLE 22-continued

| | aqueous liquid composition No. | peptide concentration | excipient | 40° C., 4 weeks later | |
|---|---|---|---|---|---|
| | | | | content of oxidized peptide | inhibition ratio of oxidized product |
| Example 34 | 34 | 0.01 mg/mL | 1 mM malic acid | 0.90% | 62% |
| Comparative Example 16 | 54 | 0.01 mg/mL | 1 mM sodium dihydrogen phosphate | 2.15% | 9% |

As shown in Table 22, it could be confirmed that the excipient in the present invention shows an inhibition effect for oxidation even when the peptide concentration of the aqueous liquid composition is low.

[Preparation of Aqueous Liquid Composition]

[Example 45], [Comparative Example 25]

In the same manner as in Example 1, the amounts described in Table 23 were prepared, filled in vials, and the vials were sealed with a butyl rubber stopper, whereby aqueous liquid compositions 69 and 70 were obtained.

TABLE 23

| | Example 45 | Comparative Example 25 |
|---|---|---|
| | aqueous liquid composition No. | |
| | 69 | 70 |
| peptide (1) [mg/mL] | 50 | 50 |
| tartaric acid [mM] | 100 | — |
| sodium dihydrogen phosphate [mM] | — | 100 |
| hydrochloric acid/sodium hydroxide | q.s. | q.s. |
| pH | 4.5 | 4.5 |

[Experimental Example 8] Stability Evaluation (7)

100 μL of 0.3% $H_2O_2$ water was added to 1 mL of the prepared aqueous liquid composition. After the mixture was lightly stirred, the content of oxidized peptide, which was the peptide resulting from oxidation of a methionine residue, was immediately measured. The content of oxidized peptide was measured by a method similar to that for stability evaluation (1).

Among the aqueous liquid compositions obtained in Examples and Comparative Examples, the contents of oxidized peptide (%) after adding 100 μL of 0.3% $H_2O_2$ to 1 mL of each of Comparative Examples 17, 18 described in Table 13, Example 45 and Comparative Example 25 described in Table 23, and Example 35 described in Table 8 are shown in Table 24. The inhibition ratio of oxidized product in the Table was calculated by the following formula.

Inhibition ratio of oxidized product (%)={(content of oxidized peptide in control sample (Comparative Example 17))−(content of oxidized peptide in Example or Comparative Example in Table 13, Table 23 or Table 8)}×100/(content of oxidized peptide in control sample (Comparative Example 17))

A higher numerical value of inhibition ratio of oxidized product means a higher inhibition effect for oxidation, and a high stabilizing effect of the excipient for peptide (1).

TABLE 24

| | aqueous liquid composition No. | peptide concentration | excipient | after addition of hydrogen peroxide | |
|---|---|---|---|---|---|
| | | | | content of oxidized peptide | inhibition ratio of oxidized product |
| Comparative Example 17 (control) | 55 | 50 mg/mL | None | 6.59% | — |
| Example 35 | 35 | 50 mg/mL | 10 mM tartaric acid | 5.07% | 23% |
| Example 45 | 69 | 50 mg/mL | 100 mM tartaric acid | 5.43% | 18% |
| Comparative Example 18 | 56 | 50 mg/mL | 10 mM sodium dihydrogen phosphate | 6.20% | 5.9% |
| Comparative Example 25 | 70 | 50 mg/mL | 100 mM sodium dihydrogen phosphate | 6.89% | −4.6% |

As shown in Table 24, it could be confirmed that the excipient in the present invention shows an inhibition effect for oxidation even when the peptide concentration of the aqueous liquid composition is high.

[Experimental Example 9] Stability Evaluation (8)

Among the prepared aqueous liquid compositions, 100 μL of 0.3% $H_2O_2$ water was added to 1 mL of each of the aqueous liquid compositions of Comparative Example 20 described in Table 14, and Examples 36, 37 and 38 described in Table 9. After the mixture was lightly stirred, the content of oxidized peptide, which was the peptide resulting from oxidation of a methionine residue, was immediately measured. The content of oxidized peptide was measured by a method similar to that for stability evaluation (1).

Among the aqueous liquid compositions obtained in Examples and Comparative Examples, the contents of oxidized peptide (%) after adding 100 μL of 0.3% $H_2O_2$ to 1 mL of each of Comparative Example 20 described in Table 14, and Examples 36, 37 and 38 described in Table 9 are shown in Table 25. The inhibition ratio of oxidized product in the Table was calculated by the following formula.

Inhibition ratio of oxidized product (%)={(content of oxidized peptide in control sample (Comparative Example 20))−(content of oxidized peptide in Example in Table 9)}×100/(content of oxidized peptide in control sample (Comparative Example 20))

A higher numerical value of inhibition ratio of oxidized product means a higher inhibition effect for oxidation, and a high stabilizing effect of the excipient for peptide (1).

TABLE 25

| | aqueous liquid composition No. | peptide concentration | excipient | after addition of hydrogen peroxide | |
|---|---|---|---|---|---|
| | | | | content of oxidized peptide | inhibition ratio of oxidized product |
| Comparative Example 20 (control) | 58 | 20 mg/mL | None | 5.08% | — |

TABLE 25-continued

| aqueous liquid composition No. | peptide concentration | excipient | after addition of hydrogen peroxide | |
|---|---|---|---|---|
| | | | content of oxidized peptide | inhibition ratio of oxidized product |
| Example 36 | 36 | 20 mg/mL | 10 mM tartaric acid + 50 mM methionine | 3.63% | 29% |
| Example 37 | 37 | 20 mg/mL | 200 mM methionine | 2.28% | 55% |
| Example 38 | 38 | 20 mg/mL | 10 mM tartaric acid + 200 mM methionine | 1.41% | 72% |

As shown in Table 25, it could be confirmed that the aqueous liquid compositions of Examples 36, 37 and 38, which were confirmed to show a CTL induction activity in Experimental Example 5, show inhibition effect for oxidation.

INDUSTRIAL APPLICABILITY

According to the present invention, a highly stable aqueous liquid composition comprising a WT1 protein-derived cancer antigen peptide can be provided, and the peptide can be easily combined with various adjuvants according to the object of use.

This application is based on U.S. provisional patent application No. 61/777,423, the contents of which are hereby incorporated by reference.

Although the present invention have been presented or described by referring to preferred embodiments of this invention, it will, however, be understood by those of ordinary skill in the art that various modifications may be made to the forms and details without departing from the scope of the invention as set forth in the appended claims. Accordingly, all such modifications are intended to be included within the scope of this invention.

All patents, patent publications and other publications identified or referenced herein are incorporated in full herein by this reference in their entireties.

---

The invention claimed is:

1. An aqueous liquid composition consisting essentially of a peptide and an excipient, and having a pH of 3-6:
   wherein the peptide is selected from the group consisting of the amino acid sequences of SEQ ID NOs: 1-7, and
   wherein the excipient consists of one or more kinds selected from the group consisting of the following (C), (D) and (E),
   (C) one or more kinds of alpha hydroxy acids selected from the group consisting of glycolic acid, lactic acid, malic acid, tartaric acid, citric acid and pharmacologically acceptable salts thereof,
   (D) one or more kinds of dicarboxylic acids selected from the group consisting of malonic acid, succinic acid, glutaric acid, maleic acid and pharmacologically acceptable salts thereof, and
   (E) methionine.

2. The aqueous liquid composition according to claim 1, wherein the peptide consists of the amino acid sequence Arg-Met-Phe-Pro-Asn-Ala-Pro-Tyr-Leu (SEQ ID NO: 1).

3. The aqueous liquid composition according to claim 1, wherein the excipient consists of both (C) and (E).

4. The aqueous liquid composition according to claim 1, wherein the excipient consists of both (C) and (E), and (C) is one or more kinds of alpha hydroxy acids selected from the group consisting of glycolic acid, lactic acid, malic acid, tartaric acid and pharmacologically acceptable salts thereof.

5. The aqueous liquid composition according to claim 1, wherein the excipient consists of both (D) and (E).

6. The aqueous liquid composition according to claim 1, wherein the excipient consists of both (D) and (E), and (D) is one or more kinds of dicarboxylic acids selected from the group consisting of succinic acid and a pharmacologically acceptable salt thereof.

7. The aqueous liquid composition according to claim 1, wherein the content per volume of alpha hydroxy acid is 1-100 mM or the content per volume of dicarboxylic acid is 10-100 mM.

8. The aqueous liquid composition according to claim 1, wherein the content per volume of methionine is 1-300 mM.

9. A method of improving stability of a peptide, consisting of the amino acid sequence shown by Arg-Met-Phe-Pro-Asn-Ala-Pro-Tyr-Leu (SEQ ID NO: 1), in an aqueous liquid composition by adding an excipient:
   wherein
   the excipient consists of one or more kinds selected from the group consisting of the following (C), (D) and (E)
   (C) one or more kinds of alpha hydroxy acids selected from the group consisting of glycolic acid, lactic acid, malic acid, tartaric acid, citric acid and pharmacologically acceptable salts thereof,
   (D) one or more kinds of dicarboxylic acids selected from the group consisting of malonic acid, succinic acid, glutaric acid, maleic acid and pharmacologically acceptable salts thereof, and (E) methionine, and wherein the aqueous liquid composition after addition of the excipient has a pH of 3-6.

10. The aqueous liquid composition according to claim 2, wherein the excipient consists of both (C) and (E).

11. The aqueous liquid composition according to claim 2, wherein the excipient consists of both (C) and (E), and (C) is one or more kinds of alpha hydroxy acids selected from the group consisting of glycolic acid, lactic acid, malic acid, tartaric acid and pharmacologically acceptable salts thereof.

12. The aqueous liquid composition according to claim 11, wherein the content per volume of alpha hydroxy acid is 1-100 mM.

13. The aqueous liquid composition according to claim 11, wherein the content per volume of methionine is 1-300 mM.

14. The aqueous liquid composition according to claim 2, wherein the excipient consists of both (D) and (E).

15. The aqueous liquid composition according to claim 2, wherein the excipient consists of both (D) and (E), and (D) is one or more kinds of dicarboxylic acids selected from the group consisting of succinic acid and a pharmacologically acceptable salt thereof.

16. The aqueous liquid composition according to claim 15, wherein the content per volume of dicarboxylic acid is 10-100 mM.

17. The aqueous liquid composition according to claim 15, wherein the content per volume of methionine is 1-300 mM.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Pro Ala Pro Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
```

```
            145                 150                 155                 160
        Gly His Thr Pro Ser His His Ala Ala Gln Phe Pro Asn His Ser Phe
                        165                 170                 175
        Lys His Glu Asp Pro Met Gly Gln Gln Gly Ser Leu Gly Glu Gln Gln
                        180                 185                 190
        Tyr Ser Val Pro Pro Val Tyr Gly Cys His Thr Pro Thr Asp Ser
                        195                 200                 205
        Cys Thr Gly Ser Gln Ala Leu Leu Leu Arg Thr Pro Tyr Ser Ser Asp
        210                 215                 220
        Asn Leu Tyr Gln Met Thr Ser Gln Leu Glu Cys Met Thr Trp Asn Gln
        225                 230                 235                 240
        Met Asn Leu Gly Ala Thr Leu Lys Gly Val Ala Ala Gly Ser Ser Ser
                        245                 250                 255
        Ser Val Lys Trp Thr Glu Gly Gln Ser Asn His Ser Thr Gly Tyr Glu
                        260                 265                 270
        Ser Asp Asn His Thr Thr Pro Ile Leu Cys Gly Ala Gln Tyr Arg Ile
                        275                 280                 285
        His Thr His Gly Val Phe Arg Gly Ile Gln Asp Val Arg Arg Val Pro
                        290                 295                 300
        Gly Val Ala Pro Thr Leu Val Arg Ser Ala Ser Glu Thr Ser Glu Lys
        305                 310                 315                 320
        Arg Pro Phe Met Cys Ala Tyr Pro Gly Cys Asn Lys Arg Tyr Phe Lys
                        325                 330                 335
        Leu Ser His Leu Gln Met His Ser Arg Lys His Thr Gly Glu Lys Pro
                        340                 345                 350
        Tyr Gln Cys Asp Phe Lys Asp Cys Glu Arg Arg Phe Ser Arg Ser Asp
                        355                 360                 365
        Gln Leu Lys Arg His Gln Arg Arg His Thr Gly Val Lys Pro Phe Gln
                        370                 375                 380
        Cys Lys Thr Cys Gln Arg Lys Phe Ser Arg Ser Asp His Leu Lys Thr
        385                 390                 395                 400
        His Thr Arg Thr His Thr Gly Lys Thr Ser Glu Lys Pro Phe Ser Cys
                        405                 410                 415
        Arg Trp Pro Ser Cys Gln Lys Lys Phe Ala Arg Ser Asp Glu Leu Val
                        420                 425                 430
        Arg His His Asn Met His Gln Arg Asn Met Thr Lys Leu Gln Leu Ala
                        435                 440                 445
        Leu

<210> SEQ ID NO 3
<211> LENGTH: 9
<212> TYPE: PRT
<213> ORGANISM: Artificial Sequence
<220> FEATURE:
<223> OTHER INFORMATION: peptide

<400> SEQUENCE: 3

Phe Met Phe Pro Asn Ala Pro Tyr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: peptide
```

```
<400> SEQUENCE: 4

Arg Met Met Pro Asn Ala Pro Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: peptide

<400> SEQUENCE: 5

Arg Met Phe Pro Asn Ala Pro Tyr Val
1               5

<210> SEQ ID NO 6
<211> LENGTH: 9
<212> TYPE: PRT
<213> ORGANISM: Artificial Sequence
<220> FEATURE:
<223> OTHER INFORMATION: peptide

<400> SEQUENCE: 6

Tyr Met Phe Pro Asn Ala Pro Tyr Leu
1               5

<210> SEQ ID NO 7
<211> LENGTH: 10
<212> TYPE: PRT
<213> ORGANISM: Artificial Sequence
<220> FEATURE:
<223> OTHER INFORMATION: peptide

<400> SEQUENCE: 7

Ala Arg Met Phe Pro Asn Ala Pro Tyr Leu
1               5                   10
```